United States Patent [19]

Tatsumi et al.

[11] Patent Number: 4,997,535
[45] Date of Patent: Mar. 5, 1991

[54] METHOD OF MANUFACTURING METHANESULFONYL CHLORIDE

[75] Inventors: Hideki Tatsumi, Akashi; Nobuo Onoda; Atsuhiro Onishi, both of Takasago, all of Japan

[73] Assignee: Toyo Kasei Kogyo Company Limited, Osaka, Japan

[21] Appl. No.: 398,340

[22] Filed: Aug. 25, 1989

Related U.S. Application Data

[63] Continuation of Ser. No. 251,015, Sep. 27, 1988, abandoned, which is a continuation of Ser. No. 33,848, Apr. 6, 1987, abandoned, which is a continuation of Ser. No. 813,271, Dec. 24, 1985, abandoned.

[30] Foreign Application Priority Data

Dec. 29, 1984 [JP] Japan .................................. 59-275078

[51] Int. Cl.$^5$ ............................................. C07C 21/00
[52] U.S. Cl. ........................ 204/157.76; 204/157.78; 204/157.79
[58] Field of Search ...................... 204/157.76, 157.78, 204/157.79

[56] References Cited

U.S. PATENT DOCUMENTS 2,174,492 12/1938 Reed ............................... 204/157.79
3,238,255 3/1966 Blackwell ....................... 204/157.79

*Primary Examiner*—John F. Niebling
*Assistant Examiner*—Isabelle McAndrews
*Attorney, Agent, or Firm*—Wenderoth, Lind & Ponack

[57] ABSTRACT

This invention is concerned with the manufacture of methanesulfonyl chloride from a mixture of methane, sulfur dioxide gas and chloride gas under irradiation of light having a wave length of 200~600 nm from a low vapor pressure mercury lamp, a high vapor pressure mercury lamp, a luminescent lamp a xenon lamp and/or sun light. High purity methanesulfonyl chloride is manufactured simply by single distillation, without using methylmercaptan which has a bad odor as raw material. The invention has special merit in utilizing sulfur dioxide gas which is produced in a large amount in the desulphurization of petroleum.

1 Claim, No Drawings

METHOD OF MANUFACTURING METHANESULFONYL CHLORIDE

This application is a continuation of now abandoned Ser. No. 07/251,015 filed Sept. 27, 1988, which is a continuation of now abandoned Ser. No. 07/033,848 filed Apr. 6, 1987, which is a continuation of now abandoned Ser. No. 06/813,271 filed Dec. 24, 1985.

BACKGROUND OF THE INVENTION

This invention is concerned with a cheap and simple method of manufacturing high quality methanesulphonyl chloride from.

A mixture of methane, sulfur dioxide gas and chlorine gas under irradiation of light. It has been known up to now that the methanesulfonyl chloride was manufactured from oxidation of methylmercaptan by chlorine gas under existence of water.

The reaction equation is given by the following chemical formula (1):

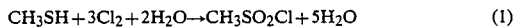

$$CH_3SH + 3Cl_2 + 2H_2O \rightarrow CH_3SO_2Cl + 5H_2O \tag{1}$$

However, this manufacturing method shown by the chemical formula (1) is not practical, because it has the following defects
(a) raw material used in this method is expensive.
(b) methylmercaptan is used as raw material, acts as a source of bad odour.
(c) Only 1/6 of chlorine gas used for the raw materials is converted into methanesulfonyl chloride, and 5/6 of the chlorine gas is spent as hydrogen chloride.

SUMMARY OF THE INVENTION

The inventors have succeeded to manufacture cheaply methanesulfonyl chloride by using a mixture of methane, sulfur dioxide gas and chlorine gas as raw materials under irradiation of light, without using solvent, and have recognized that the invention uses effectively chlorine gas and irradiated light and retards side reactions.

DETAILED DESCRIPTION OF THE INVENTION

The invention provides a method to manufacture a high purity methanesulfonyl chloride cheaply and simply from the mixture of methane, sulfur dioxide gas and chlorine gas under the irradiation of light as is shown by reaction equation (2) below:

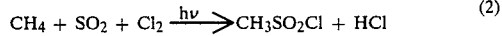

$$CH_4 + SO_2 + Cl_2 \xrightarrow{h\nu} CH_3SO_2Cl + HCl \tag{2}$$

In the invention, methane must be used 1~5-folds mols, preferably 1.1~2-fold mols per mol of chlorine gas as raw materials.

If less than 1 mol of methane is used per mol of chlorine gas, side reaction products of high boiling point are produced in large amounts compared to those produced in this invention, and it is wasteful and economically disadvantageous in this invention to use over 5 mols methane per mol of chlorine gas.

It is preferable to use high purity methane in this invention, however it is also possible to use cheap natural gas in which the main component is methane. In the case of using natural gases which include hydrocarbons other than methane in the invention, it is possible to isolate methanesulfonyl chloride simply by adding a generally used distillation process to the process of the invention.

Sulfur dioxide gas is used in an amount of 1–5 mols, preferably 1.1–3 mols, mols per mol of chlorine gas.

It is not practical to use less than 1 mold sulfur dioxide gas per mol of chlorine gas, because the side reaction product of methane chlorination is increased, and also it is wasteful and economically disadvantageous to use more than 5 mols of sulfur dioxide gas per mol of chlorine gas.

For the sources of irradiation it is not necessary to use monochromatic light, but also low vapor pressure mercury lamp, high vapor pressure mercury lamp, various general luminescent lamps, xenon lamp and moreover sunlight are also used, and most efficient range of wave length is 200~600 nm according to the research of inventors.

Necessary energy of this invention is used to convert $Cl_2 \rightarrow 2Cl$ and this necessary energy is 57~58 KCal/mol and its suitable wave length is about 500 nm. High energy light having wave length of less than 200 nm causes radical cleavage and various reactions occur and consequently the yield of methanesulfonyl chloride will become lower reaction gases are maintained at $-10°$ C.~$100°$ C. preferably $0°$ C.~$30°$ C. throughout the reaction in this reaction system.

Reaction proceeds slower as sulfur dioxide is liquified under $-10°$ C., which is not practical, and the rate at which side reactions occur becomes larger in proportion to the temperature increase the upper limit of reaction temperature is $100°$ C.

High purity methanesulfonyl chloride is obtained easily from the liquid reaction products including methanesulfonyl chloride as main ingredient by removing, small quantity of methane chlorination product, raw material gases and hydrogen chloride mixed in the main ingredient by distillation.

Obtained methanesulfonyl chloride is very useful as raw material of various industrial reagents.

Following are examples of this invention:

EXAMPLE 1

Methane, sulfur dioxide gas and chlorine gas are poured into the tublar reactor with stirrer, which has 8 cm diameter and 50 cm height made from pyrex glass. The pouring speeds of these gases into the reactor are 33 ml/min (methane) and 50 ml/min (sulfur dioxide gas) and 17 ml/min (chlorine gas) each, and the tubular reactor is irradiated by 3 20 W-blue luminescent lamps (comercial name is Toshiba F120B) from the outside of the exhausted gases are discharge from the cooler existing upper side of the reactor and the temperature is maintained at $15°$ C. inside the reactor and pouring of the gases into the reactor, and irradiation are continued for 3 hours. There consequently is obtained 14.0 g pale yellow transparent liquid and this liquid is recognized to include 81 weight percent of methanesulfonyl chloride from the result of gas chromatographic analysis, and the yield of obtained pure methanesulfonyl chloride is 72.5 weight percent based on the chloride gas used for raw material.

EXAMPLE 2

Town gas (natural gas) purified by passing through a layer of active carbon, and sulfur dioxide gas and chloride gas are introduced into the same tubular reactor from the lower side of this reactor used in Example 1.

The pouring speeds of these materials are 33 ml/min (methane), 50 ml/min (sulfur dioxide gas) and 17 ml/min (chlorine gas). They are irradiated equally as in case of Example 1, and the exhausted gases are discharged from the cooler existing upper side of the reactor. Temperature is maintained at 15° C. inside the reactor, and the pouring of the gases into the reaction vessel and irradiation are continued for 3 hours. There is obtained 13.3 g pale yellow transparent liquid, and this liquid is recognized to include 81 weight% methanesulfonyl chloride from the result of gas chromatographic analysis, and the purity of obtained pure methanesulfonyl chloride is 67.3 weight% based on the chloride gas used for raw material.

EXAMPLE 3

Methane, sulfur dioxide gas and chlorine gas are poured into the lower part of the tubular reactor, using the same reaction vessel as Examples 1 and 2, and pouring speeds of these gases are 33 ml/min (methane), 50 ml/min (sulfur dioxide gas) and 17 ml/min (chlorine gas). Exhausted gases are discharged from the cooler existing upper part of the tubular reactor. The tubular reactor is exposed to sunlight at the same time when gases are poured into the reaction vessel, and pouring is continued for 4.5 hours. The gases in the reactor are maintained at 10° C. and there is obtained pale yellow transparent liquid of 206 g and liquid in an amount is recognized to include 75 weight percent of methanesulfonyl chloride from the result of gas chromatographic analysis, and the yield of obtained pure methanesulfonyl chloride is 65.8 weight% based on the chlorine gas used for raw material.

The method of this invention has many effects compared to the ordinary method of manufacturing methanesulfonyl chloride, i.e.

(a) high utility of raw material,
(b) this invention does not use methylmercaptan which is expensive and gives a source of bad odor as raw material, and
(c) the invention uses sulfur dioxide gas which is produced in large amount when petroleum is desulfurized and/or the like.

We claim:

1. A method of manufacturing methanesulfonyl chloride, which comprises:

introducing methane-containing natural gas, sulfur dioxide gas and chlorine gas as starting materials in to the lower portion of a tubular reactor at a rate of 33 ml/min for the methane, 50 ml/min for the sulfur dioxide gas and 17 ml/min for the chlorine gas in a $CH_4:Cl_2$ mole ratio of 2-5:1 and a $SO_2:Cl_2$ mole ratio of 1.1-3:1 in the absence of solvent, adjuvant and diluent; and irradiating the resultant mixture of said starting materials for 3 to 4.5 hours with light from a source outside said reactor selected from the group consisting of a low vapor pressure mercury lamp, a high vapor pressure mercury lamp, a luminescent lamp, a xenon lamp and sunlight having a wave length of 200-600 nm, while maintaining the temperature of said starting materials in said reactor at 10° to 15° C. and discharging exhausted gases from a cooler existing upper side of said reactor, to produce said methanesulfonyl chloride by means of gas phase reaction.

* * * * *